United States Patent [19]
Senkeleski et al.

[11] Patent Number: 5,562,937
[45] Date of Patent: Oct. 8, 1996

[54] AMYLASE-TREATED WAXY STARCH IN FOODS AND PROCESS OF MAKING

[75] Inventors: Jamie Senkeleski, Neshanic Station; Chung-Wai Chiu, Westfield; Zu-Feng Xu; William R. Mason, both of Somerville; Karen L. Chicalo-Kaighn, Clifton, all of N.J.

[73] Assignee: National Starch and Chemical Investment Holding Corporation, Wilmington, Del.

[21] Appl. No.: 358,483

[22] Filed: Dec. 19, 1994

[51] Int. Cl.$^6$ .................................................. A23L 1/0522
[52] U.S. Cl. .......................... 426/48; 426/549; 426/603; 426/613
[58] Field of Search ............................. 426/48, 549, 603, 426/613

[56] References Cited

U.S. PATENT DOCUMENTS

| | | | |
|---|---|---|---|
| 3,525,672 | 8/1970 | Wurzburg et al. | 195/31 |
| 3,644,126 | 2/1972 | Bodnar et al. | 426/48 |
| 3,868,464 | 2/1975 | Koaze et al. | 426/48 |
| 4,009,291 | 2/1977 | Mitchell et al. | 426/548 |
| 4,427,701 | 1/1984 | Morley | 426/36 |
| 4,510,166 | 4/1985 | Lenchin et al. | 426/565 |
| 4,624,853 | 11/1986 | Rudin | 426/61 |
| 4,780,149 | 10/1988 | Kaper et al. | 127/38 |
| 4,837,035 | 6/1989 | Baker et al. | 426/43 |
| 4,837,036 | 6/1989 | Baker et al. | 426/43 |
| 4,855,149 | 8/1989 | Pucci et al. | 426/48 |
| 4,877,634 | 10/1989 | Pucci et al. | 426/531 |
| 4,925,795 | 5/1990 | Takasaki | 426/48 |
| 4,977,252 | 12/1990 | Chiu | 536/102 |
| 5,266,467 | 11/1993 | Inglett | 435/99 |

FOREIGN PATENT DOCUMENTS

| | | |
|---|---|---|
| 40013/93 | 1/1993 | Australia . |
| 0289138A3 | 11/1988 | European Pat. Off. . |
| 0529892A1 | 3/1993 | European Pat. Off. . |
| 0574721A1 | 12/1993 | European Pat. Off. . |
| 51-088645 | 3/1976 | Japan . |
| 51-079750 | 7/1976 | Japan . |
| 1273593 | 1/1989 | Japan . |
| 1252296 | 6/1989 | Japan . |
| 5-004072 | 1/1993 | Japan . |
| 5-037036 | 6/1993 | Japan . |

OTHER PUBLICATIONS

Pierre Würsch and Didier Gumy, "Inhibition of amylopectin retrogradation by partial beta–amylolysis", *Carbohydrate Research*, 256 (1994) pp. 129–137, Elsevier Science B.V., Amsterdam.

Leland Dahle, Vincent Brusco and Gary Hargus, "Some Effects of Beta Amylolytic Degradation of Pastes of Waxy Maize Starch", Journal of Food Science–vol. 38 (1973).

*Primary Examiner*—Helen Pratt
*Attorney, Agent, or Firm*—Karen G. Kaiser

[57] ABSTRACT

A formulated starch-containing food product characterized by improved mouth-feel and texture is prepared from a mixture of non-starch ingredients together with a beta-amylase or glucoamylase treated waxy starch which has been prepared by a process which comprises steam cooking a starch slurry at a temperature of 120° to 170° C. to completely gelatinize the waxy starch; enzymatically hydrolyzing the gelatinized starch with beta-amylase or glucoamylase until up to about 60% by weight of the starch has been degraded to maltose or glucose; terminating the enzyme degradation by deactivating the enzyme and recovering the starch by spray drying.

7 Claims, No Drawings

AMYLASE-TREATED WAXY STARCH IN FOODS AND PROCESS OF MAKING

BACKGROUND OF THE INVENTION

For many food products, the mouth-feel or texture perceived by the consumer is a critical factor. These properties are often found lacking in the case of food products which have been modified so as to remove certain conventional components thereof in an effort, for example, to lower the sugar or fat content of the resultant product.

For example, yogurt is conventionally a cultured milk product produced by fermenting sources of butterfat, such as milk, skim milk, cream, nonfat milk solids and the like in liquid or powder form with a yogurt culture producing lactic acid. Much of the texture, body and mouth-feel of the yogurt product is a consequence of the level of butterfat used in the fermentation, with higher butterfat sources producing the most desirable products. Thus, as efforts have been made to produce lower calorie yogurt derived from lower butterfat sources, various attempts have been made to improve the mouth-feel and texture thereof.

Similar needs are encountered in the production of other low fat foods such as reduced calorie spoonable salad dressings, sour cream, frozen desserts and the like. Further, the substitution of aspartame or other artificial sweeteners for sugar in marinades, dry mixes and beverages has also provided a need for an additive to improve the mouth-feel or "texture" of the final product.

In addition to the need in the industry to improve the mouth feel or texture of certain food products, there is a concurrent need to do so without the use of chemical modifiers or other additives which might either require regulatory approval or revision of the natural labelling status of the product.

SUMMARY OF THE INVENTION

We have now found that the use of beta-amylase or glucoamylase treated waxy starch in food systems containing little or no fat significantly improves the mouth-feel and texture of the product while also contributing to the texture thereof. Moreover, since the starch is comprised solely of maltose or glucose and enzyme-modified starch, it is FDA acceptable and there is no necessity to revise the labels on the final products.

More specifically, we have found that a waxy starch which has been steam cooked, then digested with beta-amylase or glucoamylase, followed by spray drying may be incorporated into products such as cultured yogurt, sour cream, soft serve desserts, spoonable salad dressing, bread spread, etc., to provide fatty/oily mouth feel, maintain texture, improve stir-down property and provide other beneficial properties. The same starch may also be used in low sugar containing dry mixes, marinades and beverages to provide the mouth-feel properties which are lost when the sugar is reduced or removed.

DETAILED DESCRIPTION OF THE PREFERRED EMBODIMENTS

For use herein, the term "waxy starch" is meant to include a starch or flour containing at least about 95% by weight amylopectin. Examples of suitable materials include waxy maize, waxy rice, waxy barley, waxy sorghum, waxy potato as well as their corresponding flours. Converted, i.e., acid treated waxy starches may also be used as the starting materials. For reasons of availability, waxy maize is preferred.

In order to obtain the desired properties, it is necessary that the starch be steam cooked, i.e. "jet cooked", by which is meant that it is slurried and heated to temperatures of about 120° to 170° C., preferably 130° to 165° C., in order to completely gelatinize the waxy starch. The steam cooking is generally carried out in a slurry at a solids level of about 15 to 35%, preferably 18 to 23%, a pH of 5 to 7, preferably 5.0 to 5.5, with a pressure of 60 to 80 psi in the cooking chamber.

The resultant fully gelatinized starch is then enzymatically hydrolyzed with beta-amylase or glucoamylase using techniques known in the art and described, for example in U.S. Pat. Nos. 3,525,672 to Wurzburg et al. and 4,977,252 to Chiu. Generally the enzyme treatment is carried out at a solids level of about 18 to 23%, depending upon the base starch being treated. Thus, depending upon the starch as well as the reaction conditions used during the steam cooking, it may be necessary to further dilute the starch slurry prior to the enzyme reaction.

The enzyme must be an exo-enzyme, capable of cleaving the 1,4-alpha-D-glucosidic linkages from the non-reducing end of the starch molecule, without cleaving substantial portions of the 1,6-alpha-D-glucosidic linkages. Beta-amylase, which is preferred, is a very specific exo-enzyme which, by its action, is able to form a reaction complex only from the non-reducing ends of the starch molecule with a maltoside group which is linked to a glucose group via a 1,4-alpha-D-glucosidic linkage. Thus, the enzyme attacks starch only at the non-aldehydic end (the non-reducing end) thereby splitting off maltose units from these outer branches until a point of branching (a 1,6 linkage) is reached. A single maltose of glucose unit remains at each branch point of the starch molecule after enzyme treatment. Since this exo-enzyme is capable of splitting the 1,4 linkages of the starch molecule but is not capable of splitting the 1,6 linkages, the residue of such degradation procedure is a compact molecular structure which is substantially free of outer branches or contains shortened outer branches. Alternatively, glucoamylase, an exo-enzyme which attacks the 1,4 linkages but also has limited activity with respect to the 1,6 linkages and results in the production of glucose and fragmented starch units may also be used.

The enzyme reaction is continued until at least 5% and up to about 60% (preferably 15 to 35%), by weight, of the starch has been degraded to maltose or glucose, or until the desired end point (i.e., sufficient degradation to provide the desired functionality for the particular application) has been reached. The end point may be determined by change in viscosity, by reducing sugar content, or by any other method known in the art for measuring the level of enzyme degradation of the starch molecule. Ordinarily the degradation will be carried out for periods ranging from a few hours to 24 hours or more depending on the temperature, enzyme and substrate concentrations, and other variables. The enzyme degradation is then terminated by raising the temperature to 85° to 95° C. and maintaining it at that temperature for at least 15 minutes to fully deactivate the enzyme.

The resulting treated starch is then recovered by conventional spray drying techniques. It can be used directly in various food products including, but not limited, to yogurt, sour cream, soft serve desserts, spoonable salad dressing, sandwich or bread spread, etc., to provide fatty/oily mouth feel, maintain texture, improve stir-down property and provide other beneficial properties. The same starch may also be used in reduced sugar dry mixes, marinades and beverages to provide the mouth-feel properties which are lost when the sugar is reduced or removed.

Depending upon the intended end use, the particular viscosity of the starch will vary. Thus, for highly thickened formulations such as yogurt, sour cream and spoonable dressings, higher viscosity products are preferred while for beverages and the like, the lower viscosity levels are optimal. The ultimate viscosity of the treated starch depends on a number of factors including, but not limited to, the type of waxy starch used, the initial viscosity of the starch cook, as well as the length of the enzyme treatment, i.e. the degree of enzyme conversion.

EXAMPLE I

Using the following procedure a beta-amylase treated starch was prepared. The resultant starch was then formulated into various food products as described in the Examples which follow.

Ten kg of Amioca were slurried in 25 L of water and then steam cooked to produce a starch dispersion of 20 to 23% solid with about 175 seconds of funnel viscosity at 10% solids and 22° C. The slurry was cooled down to 50° to 55° C. in a reaction tank. Then 2.5 g of β-amylase solution (1300 U/g) were added to the starch for amylolytic digestion. Once the desired viscosity or dextrose equivalent value was reached, the reaction was stopped by rapidly heating the dispersion to 85° C. The dispersion was spray-dried to obtain a powdered product.

EXAMPLE II

A low-fat yogurt was prepared from the formulation listed below by (1) blending the dry ingredients and adding them to the milk with a waring blender (rpm between 20 to 30); (2) the mixture is pasteurized at 82° C. and held for 10 minutes; (3) homogenize mixture at 1500 psi using APV Gaulin 2-stage homogenizer; (4) cool the product to 49° C.; (5) add 1.5% starter culture to the mixture; (6) incubate product at 45° C. until a pH of 4.7±0.05 or titratable acidity of 0.90 is a (7) after incubation store products at 4° C.; (8) cool products as quickly as possible to slow lactic acid producing bacteria.

| Yogurt with enhanced mouth-feel and improved texture: | |
|---|---|
| Ingredients | % weight |
| 1% fat milk | 90.0 |
| Nonfat dry milk | 6.0 |
| Starch of Ex. 1 | 2.0 |
| 10 DE maltodextrin | 2.0 |

A control sample was also prepared containing 4.0% 10 DE (dextrose equivalence) Maltodextrin in place of the beta-amylase treated starch. The yogurt made with the Beta-amylase treated starch of Example I had similar characteristics to a full-fat cultured yogurt. This starch provided a smooth, creamy, slippery mouth-feel. Visually when the product was stirred, the texture maintained a homogenous consistency without lumps. In contrast, the yogurt containing only the maltodextrin exhibited a quick melt-away, lacked body and did not provide a mouth-coating.

EXAMPLE III

A non-fat soft serve ice cream was prepared from the formulation listed below by (1) blending together milk, corn syrup and stabilizer with a no-shear Baldo Mixer (a Lightin' Mixer type unit)' (2) dry blend sugar, starch and nonfat dry milk and add to milk mixture; (3) continue mixing with Baldo Mixer; (4) the mixture is pasteurized at 71° C. for 30 minutes; (5) homogenize the mixture at 3000 psi using APV Gaulin 2-stage homogenizer; (6) cool product to 4° C.; (7) freeze the dessert to -8° C. to approximately 80% overrun.

| Non-fat soft serve ice cream formulation: | |
|---|---|
| Ingredients | % weight |
| Skim milk | 75.3 |
| Sugar | 10.0 |
| Corn syrup (36 de) | 6.0 |
| Nonfat dry milk | 5.9 |
| Starch of Ex. 1 | 2.0 |
| Stabilizer | 0.85 |

The starches described below were evaluated in the non-fat soft serve ice cream. Each sample was visually evaluated for texture and organoleptic quality. The β-amylase treated starch provided the soft ice cream with fat replacement properties, such as, excellent mouth-feel properties, slow melt rate and smooth and creamy texture. The mix viscosity remained stable over time and desired percent overrun was easily achieved.

EXAMPLE IV

The beta-amylase treated starch also provides mouth-feel enhancement to reduced and non-fat sour cream. A no-fat sour cream was prepared from the formulation listed below by (1) blending the dry ingredients and adding them to the milk with a waring blender (rpm between 20 to 30); (2) the mixture is pasteurized at 74° C. and held for 30 minutes; (3) homogenize mixture at 2500 psi using APV Gaulin 2-stage homogenizer; (4) cool the product to 22° to 23° C.; (5) inoculate with culture (85 grams per 200 gallons); (6) incubate product at 22° to 26° C. until a pH of 4.7±0.05 or titratable acidity of 0.75 is achieved; (7) after incubation store products at 4° C.; (8) cool products as quickly as possible to slow lactic acid producing bacteria.

| Non-fat sour cream: | |
|---|---|
| Ingredients | % weight |
| Skim milk | 87.92 |
| Nonfat dry milk | 5.0 |
| Stabilizer | 3.0 |
| Specialty Starch of Ex. I | 4.0 |
| Sodium citrate | 0.08 |

EXAMPLE V

Similar favorable results were achieved using the Beta-amylase treated starch in the following formulations:

| Pancake syrups: | |
|---|---|
| Ingredients | Weight % |
| Starch of Ex. 1 | 24.7 |
| Sugar | 20.0 |
| High fructose corn syrup | 40.3 |
| Water | 1.5 |
| Maple syrup | 2.5 |
| Potassium sorbate | 0.1 |
| Caramel color | 0.03 |

Disperse the beta-amylase treated starch in the high fructose corn syrup and water mix.

Heat the slurry to 88° C. and hold for 10 minutes.

Add the caramel solution previously diluted with some of the water in the formulation.

Add the remaining ingredients and hold for another 2 minutes at 88° C.

Hot fill the glass bottles with the syrup and cap.

| No-fat chocolate sauce: | |
|---|---|
| Ingredients | Weight % |
| Water | 34.2 |
| Sugar | 32.9 |
| 42 DE Corn syrup | 20.4 |
| Milk solids non-fat | 6.7 |
| Purity W, modified food starch | 1.7 |
| Cocoa powder | 1.5 |
| Caramel color | 1.2 |
| Starch of Ex. I | 1.0 |
| Salt | 0.2 |
| Potassium sorbate | 0.2 |

EXAMPLE VI

An experiment was conducted to determine the contribution β-amylase treated waxy starch provides with regard to mouth-feel enhancement in a low sugar beverage system. The beverage was prepared as follows: 1) Disperse the starch in already prepared beverage drink (the drink contained no additives that would provide additional mouth-feel). 2) Heat in the microwave oven for 2 minutes on high. 3) Add water to make up to the original weight. 4) Cool the solutions to approximately 25° C.

| FORMULATION FOR BEVERAGE WITH ENHANCED MOUTH-FEEL | |
|---|---|
| INGREDIENTS | % WEIGHT |
| Beverage Drink | 98.00 |
| Starch | 2.00 |

The starch was evaluated in the beverage drink for mouth-feel enhancement. Four trained panelists participated in the sensory test.

The addition of β-amylase treated waxy starch to a beverage drink enhanced the mouth-feel and provided added body. The starch also rounded off the acidity and gave the beverage a smoother flavor profile. In contrast, the control sample prepared with 2 parts of 10 DE Maltodextrin provided little mouth-feel, watery, weak, thin, very similar to control, no enhancement in body, while the Control prepared with no additives had little mouth-feel and was tart, thin and watery.

EXAMPLE VII

The β-amylase treated starches of the invention also provide mouth-feel enhancement in dry mix beverages.

A no-fat dry mix shake was prepared from the formulation listed below by (1) blend all dry ingredients together; (2) add dries to water and disperse in waring blender; (3) blend for 3 minutes or until fully dispersed; (4) chill in refrigerator.

| NON-FAT CHOCOLATE DRY SHAKE MIX | |
|---|---|
| INGREDIENTS | % WEIGHT |
| Water | 74.50 |
| Milk Solids Non-Fat | 12.00 |
| Sugar | 8.50 |
| Starch of Ex. I | 2.50 |
| Cocoa Powder | 2.00 |
| Vanilla Powder | 0.50 |

EXAMPLE VIII

The following describes preparation of a control (full-fat) and two no-fat dressings, containing, respectively, the beta-amylase treated starch of Example I (Test 1) and no fat replacer (Blank).

1. Blend dry ingredients and add to vinegar and water
2. Kettle cook 10 minutes at 195° F.
3. Cool to 80° F.
4. In the case of the control full-fat dressing, slowing add the oil to the cooled paste while mixing with a wire whip.
5. Colloid mil at 0.060".
6. Pack

| Ingredients | Control | Test 1 | Blank |
|---|---|---|---|
| Vinegar (120 Grain) | 8.6% | 7.0% | 7.0% |
| Water | 33.0 | 74.74 | 74.74 |
| THERMFLO, modified food starch | 3.4 | 6.5 | 6.5 |
| Starch of Ex. I | | 2.0 | |
| 10 DE maltodextrin | | | 2.0 |
| Sugar | 5.0 | 5.0 | 5.0 |
| Whey protein concentrate | 3.0 | 3.0 | 3.0 |
| Salt | 1.5 | 1.5 | 1.5 |
| Mustard powder | 0.5 | 0.5 | 0.5 |
| Sodium benzoate | | 0.08 | 0.08 |
| Potassium sorbate | | 0.08 | 0.08 |
| Citric Acid | | 0.1 | 0.1 |
| Ethylene diamine tetracetate | | 0.0075 | 0.0075 |
| Vegetable Oil | 45.0 | | |
| TOTAL | 100.00 | 100.00 | 100.00 |

Relative to the blank without the fat replacer, the Test 1 sample will be more oily and rich in mouth-feel, more like the control. Further, the Test 1 dressing did not increase in viscosity during 2 months refrigerated storage.

EXAMPLE IX

In order to demonstrate the criticality of the processing techniques described herein to the effects on the food product, a beta-amylase treated starch was prepared using the process described in Australian Patent Application A-40013/92 to Gumy et al. wherein the untreated starch is batch cooked at temperatures of only to 65°–75° C., a temperature range which only partially gelatinizes the starch and wherein the beta-amylase treated starch is then recovered by drum drying.

When formulated into the yogurt product described in Example II above, the yogurt containing the starch treated according to the Australian application exhibited no stir down properties, was chunky rather than smooth in texture and had an unpleasant taste and mouth-feel.

We claim:

1. A formulated starch-containing food product characterized by improved mouth-feel and texture comprising a mixture of non-starch ingredients together with a beta-amylase or glucoamylase treated waxy starch which has been prepared by a process which comprises steam cooking a starch slurry at a temperature of 120° to 170° C. to completely gelatinize the waxy starch; enzymatically hydrolyzing the gelatinized starch with beta-amylase or glucoamylase until up to about 60% by weight of the starch has been degraded to maltose or glucose; terminating the enzyme degradation by deactivating the enzyme and recovering the starch by spray drying.

2. The food product of claim 1 wherein the starch has been steam cooked at a temperature of 130° to 165° C.

3. The food product of claim 1 wherein the waxy starch is waxy corn.

4. The food product of claim 1 comprising a non-fat cultured yogurt.

5. The food product of claim 1 comprising a non-fat sour cream.

6. The food product of claim 1 comprising a beverage.

7. A process for treating waxy starch comprising the steps of:

a) steam cooking a slurry of the waxy starch at a temperature of 120° to 170° C. to completely gelatinize the starch;

b) enzymatically hydrolyzing the gelatinized starch with beta-amylase or glucoamylase until up to about 60% by weight of the starch has been degraded to maltose or glucose;

c) terminating the enzyme degradation by deactivating the enzyme; and d) recovering the starch by spray-drying.

* * * * *